United States Patent [19]  [11] Patent Number: 5,578,008
Hara  [45] Date of Patent: Nov. 26, 1996

[54] HEATED BALLOON CATHETER

[75] Inventor: Shinji Hara, Tokyo, Japan

[73] Assignee: Japan Crescent, Inc., Japan

[21] Appl. No.: 136,644

[22] Filed: Oct. 14, 1993

Related U.S. Application Data

[63] Continuation-in-part of Ser. No. 984,490, Dec. 2, 1992, abandoned.

[30] Foreign Application Priority Data

Apr. 22, 1992 [JP] Japan ................................. 4-103230
Apr. 22, 1992 [JP] Japan ................................. 4-103231

[51] Int. Cl.$^6$ ............................................ A61M 29/00
[52] U.S. Cl. ............................... 604/96; 604/21; 606/27
[58] Field of Search ................................ 604/96, 20, 21, 604/113, 97–100, 102, 103; 606/28, 27, 29, 192, 194; 128/658; 607/123, 125

[56] References Cited

U.S. PATENT DOCUMENTS

| 4,512,762 | 4/1985 | Spears . | |
|---|---|---|---|
| 4,773,899 | 9/1988 | Spears . | |
| 4,799,479 | 1/1989 | Spears . | |
| 4,860,744 | 8/1989 | Johnson et al. | 606/31 |
| 4,878,492 | 11/1989 | Sinofsky et al. . | |
| 4,955,377 | 9/1990 | Lennox et al. | 606/27 X |
| 5,019,075 | 5/1991 | Spears et al. . | |
| 5,047,025 | 9/1991 | Taylor et al. . | |
| 5,092,841 | 3/1992 | Spears . | |
| 5,236,413 | 8/1993 | Feiring | 604/21 |
| 5,344,398 | 9/1994 | Hara | 604/96 |
| 5,417,689 | 5/1995 | Fine | 606/41 |

FOREIGN PATENT DOCUMENTS 4-338472  5/1992  Japan .

Primary Examiner—Randall L. Green
Assistant Examiner—V. Alexander
Attorney, Agent, or Firm—Quarles & Brady

[57] ABSTRACT

Disclosed is a heated balloon catheter in use for effectively heating of the constricted zone of blood vessels deep thereinto, performing a proper temperature measurement, having further advantage of easy fabrication thereof.

A 2 to 20 MHz radio frequency generator is connnected to heating electrode within a balloon and opposite electrode external of a patient respectively. A thermocouple mounted within the balloon is connected to an external temperature controller across paired conductors. A passive filter and an active filter are provided to eliminate said R.F. noise from said conductors. From R.F. generator is supplied R.F. energy to allow the capacitive current to flow through the patient's body via the electrodes, whereby a stenosis can be heated deep thereinto by capacitive heating. From the thermocouple is output the D.C. thermoelectric potential corresponding to the temperature to the temperature controller, of which the siganals are purified by said filters. Further disclosed are catheters including two conductor wires, together with one wire and no wire structrues respectively.

17 Claims, 11 Drawing Sheets

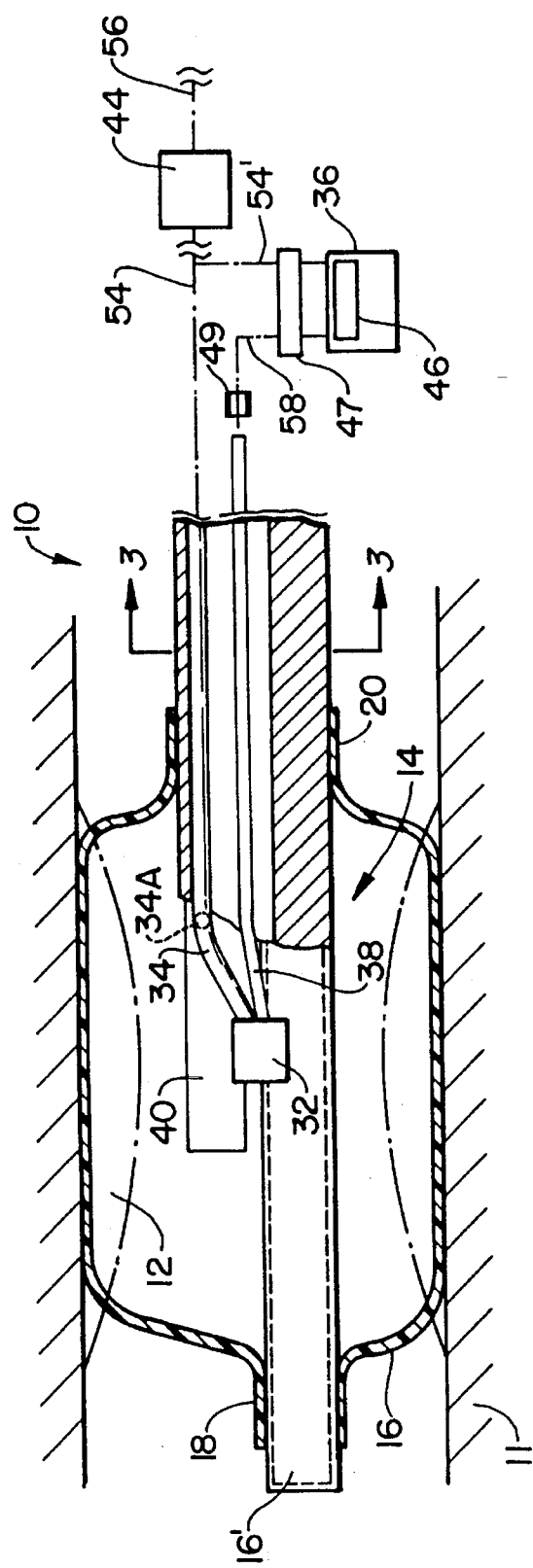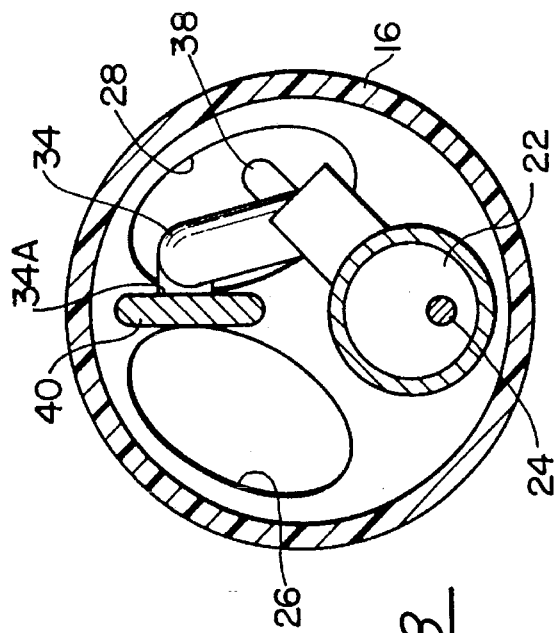
FIG. 7
FIG. 8

HEATED BALLOON CATHETER

CROSS REFERENCE TO RELATED APPLICATIONS

This application is a continuation-in-part of application U.S. Ser. No. 07/984,490 filed Dec. 2, 1992, now abandoned. The pending application hereinabove is incorporated herein and is a part hereof.

BACKGROUND OF THE INVENTION (a) Field of the Invention

The present invention relates to a heated balloon catheter having utitlity in a number of fields for treatment of humans, for example, elimimation or reducing atherosclerosis; heart valve stenosis; dilatation of the prostate, esophagus, and hepatic duct, etc.

The invention will be specifically described in respect to percutanous tramsulumenal coronary angioplasty (PTCA).

(b) Description of Prior Art

Hot balloon catheters are known in the art for PTCA treatment wherein cardiac catheterization is carried out by directing an inflatable balloon in a coronary artery in the region of a coronary narrowing, and U.S. patents disclosing such treatment are Lennox U.S. Pat. No. 5,047,025, Taylor U.S. Pat. No. 5,047,025, and Johnson U.S. Pat. No. 4,860,744.

However, the above each Patents employs two wires inserted into the catheter for bipolar heating systems in use for the heating of the liquid within a balloon, therefore, blood vessels cannot be heated deep thereinto. Additionally, proper measurement of the temperature within a balloon and mass production of hot balloon catheters have been difficult because of relatively difficult fabrication thereof.

SUMMARY OF THE INVENTION

Accordingly, it is the main object of the present invention to provide a heated balloon catheter which is able to efficiently heat blood vessels deep within the constricted zones thereof.

It is another object of the present invention to provide a heated balloon catheter for which it is possible to properly measure the temperature within the balloon.

It is a further object of the present invention to provide a heated balloon catheter which is easily fabricated.

In accordance with a major feature of the present invention, there is provided a structure for a heated balloon catheter comprising:

a thermocouple sensor provided within the balloon;

paired electrical conductors for connecting the thermocouple sensor to an extenal temperature controller;

a heating internal electrode mounted within the balloon;

an external electrode provided outside the balloon;

an R.F. generator external of the catheter for supplying radio frequency energy in the order of 13.56 MHz heating electrical conductors for connecting said R.F. generator to said internal heating electrode and external electrode so that the capacitive heating may be caused within a patient's body through said electrodes;

a noise filtering means for rejecting said 13.56 MHz noise in said electrical conductor connected to said temperature sensor;

and a impedance matching network to fine tune the impedance of the circuitry including the catheter.

BRIEF DESCRIPTION OF THE DRAWINGS

Other objects, features and advantages of the invention will be apparent to those skilled in the art from the following description of the preferred embodiment of the invention, wherein reference is made to the accompanying drawings, of which:

FIG. 7 is a fragmentary sectional view of the distal end of a thermal PTCA balloon catheter of the present invention, including two wires therein, also illustrating certain of the electrical components such as the R.F. generator and temperature controller.

FIG. 8 is a section of the distal end of the catheter of the second embodiment of the invention.

DESCRIPTION OF A PREFERRED EMBODIMENT

Hereinafter is described a first embodiment of the present heated balloon catheter with reference to FIGS. 1 to 6, in which the cathter includes 3 wires therein.

Figure 1:
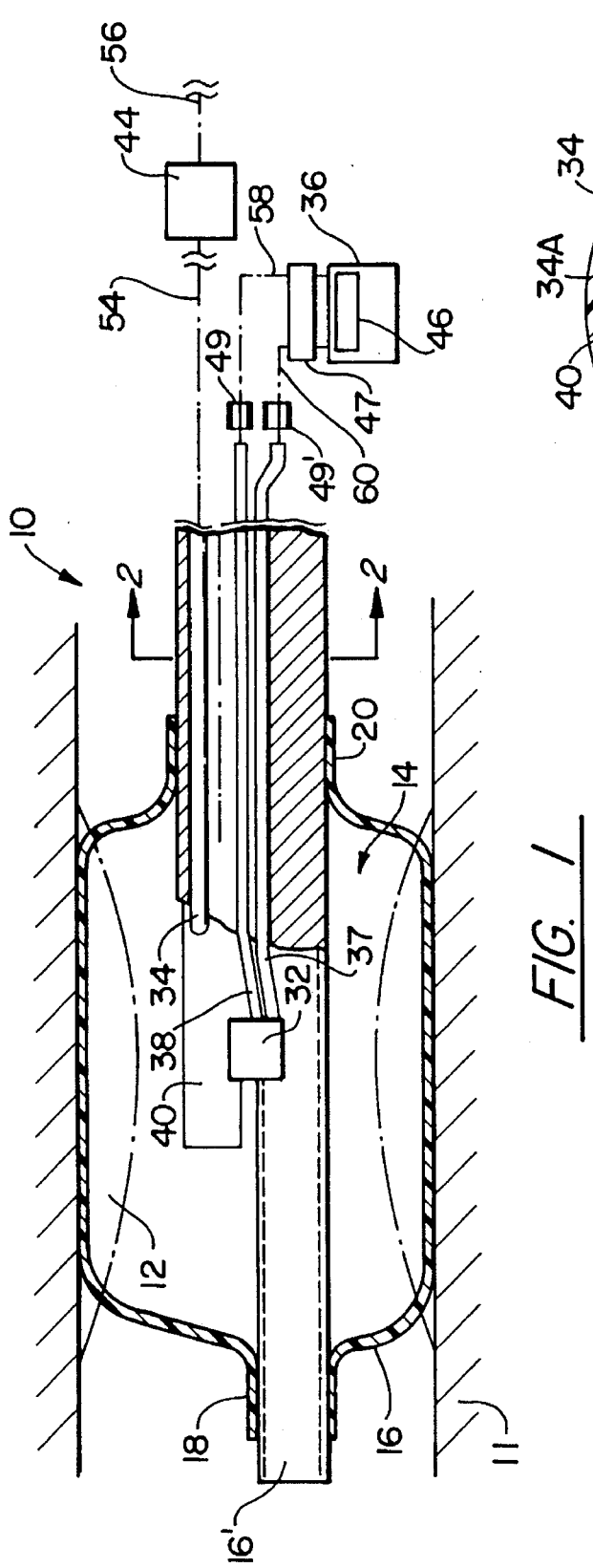
FIG. 1 is a fragmentary sectional view of the distal end of a thermal PTCA balloon catheter of the present invention, including three wires therein, also illustrating certain of the electrical components such as the R.F. generator and temperature controller.

Referring to FIG. 1 of the drawings, 10 generally designates the distal end of a thermal PTCA balloon catheter. Reference number 11 is an artery having a region of stenosis designated as 12.

Into the region is inserted the distal end of the balloon catheter, generally designated 14, which includes a thin-walled balloon 16.

Mechanical strength of a balloon is not particularly important with the present PTCA catheter, since the present invention can dilate the stenosis at much lower pressure, as 2–8 atm, while conventional balloon catheters now dilate at 10–15 atm. Additionally, the present PTCA catheter enables clinical doctors to properly measure the temperature within the catheter 16 in order to moderately heat the stenosis 12, so that doctors can successfully dilate the same, whereby late re-stenosis and the damage to the tissue of blood vessesls can be prevented, which is one of the reasons that the hot balloon catheter PTCA is very attractive for doctors.

Typically, the membrane should be less than 20 microns, while, sometimes, up to 100 microns are used for a balloon where a stronger wall is necessary. The balloon is usually constructed of polyethylene telephthalate or polyethylene, while other materials, such as urethane, may be employed.

The balloon is sealed, at its ends 18 and 20, to a, preferably, three-passage (i.e. 22,26,28) catheter tube 16'. The catheter tube 16', in the illustrated form of the invention, has said three passages, the first passage of about 400 micron I.D. for the feed-in-and-feed-out of a fluid designated as 26, the second passage 28 of about 500 micron I.D. for the insertion of electrical conductors thereinto, the third passage 22 about 700 micron I.D. for the insertion of an isolated guide wire 24 thereinto, as shown in FIGS. 2, 3.

Figure 2:
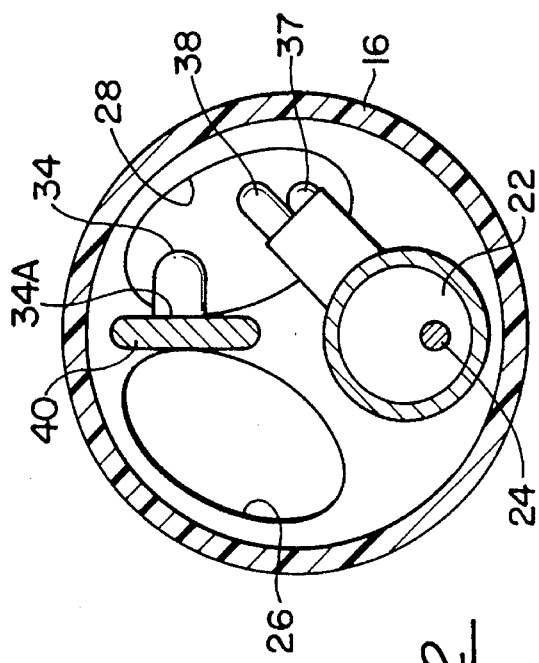
FIG. 2 is a section of the distal end of the catheter of the first embodiment of the invention.
Figure 3:
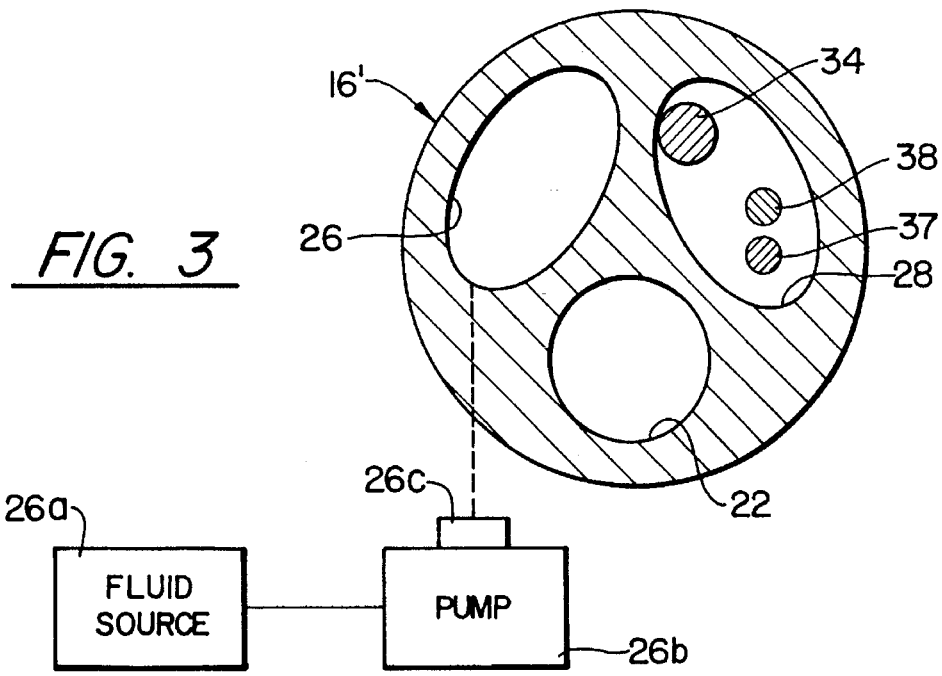
FIG. 3 is a section on line 2—2 of FIG. 1.
Figure 4:
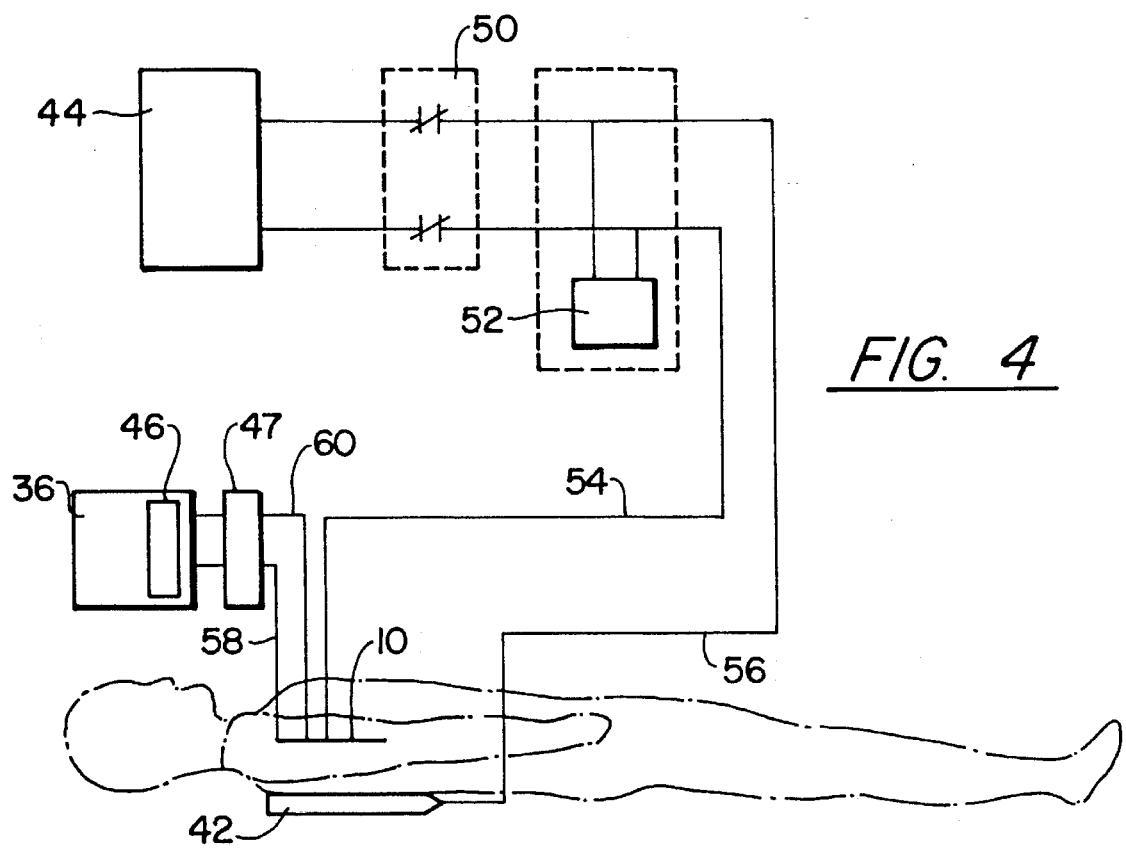
FIG. 4 is a schematic drawing showing the electrical components of the system in relationship to a human undergoing PTCA treatment.

Referring to FIGS. 1 and 2, at the distal end of the catheter is provided a thermocouple 32, as a temperature sensing means. Into the passage 28 are inserted a copper wire 34 as a heating electrical means, a copper wire 37 and constantan wire 38 as paired electrical conductors, which are welded at the ends to construct said thermocouple 32. The diameter of said copper wire 34 is, for example, 160 to 200 microns, while the diameters of said copper wire 37 and constantan wire 38 are nearly 50 microns respectively.

Said thermocouple 32 is connected to an external temperature meter 36 via the copper wire 37 and the constantan wire 38. Again referring to FIG. 2, reference number 40 designates one element of a heating electrode, to which is connected the copper wire 34 via a connector 34A. The heating electrode 40 is an antenna provided within the balloon 16. In the present invention, it is proposed that the heating electrode 40 is 200 microns in width and 10 milimeters in length to transmit the 13.56 MHz radio frequency toward the opposite electrode or terminal plate placed at the back of a patient. The opposite electrode is in contact with the patient and is designated 42, FIG. 4 of the drawings. Said electrode 40 receives energy from the radio frequency generator 44, positioned externally of the patient.

In a preferred form of the invention, the R.F. generator should be limited to a crystal-controlled oscillator.

Coupled with the system is a filtering network, in order to properly measure the temperature within the heated balloon.

In order to measure temperature where R.F. energy is used to heat the tissue aroud the balloon, one must eliminate the heating source or the 13.56 MHz R.F. signal to the temperature meter 36. A good rejection filter in the thermometer is necessary. Thus an active rejection filter 46 is connected to the temperature meter 36 in order to eliminate 13.56 MHz noise.

However, conventional active rejection filter have −100 db rejection at most at 13.56 MHz. Since active filters can filter out (reject) "noise" at a specific frequency, it is important that the noise source, that is, the R.F. energy for heating balloon, be as pure as possible, which, in this case, is crystal oscillation of 13.56 MHz.

However, since the signal level of thermocouple is in the order of micro V, whereas the peak-to-peak value of heating power of 13.56 MHz radio frequency is in the order of several hundreds of volts, thus steady temperature measurement cannot be obtained by means of the active filter alone. Therefore, certain passive filter such as radio frequency attenuating element must be provided preceding said active filter. This is a very important feature of the invention.

That is, it is imperative that, preceding the active filter, passive filters such as coil and/or high-resistance wire be employed, for filtering out the 13.56 MHz noise to obtain as pure temperature signals as possible.

Figure 5:
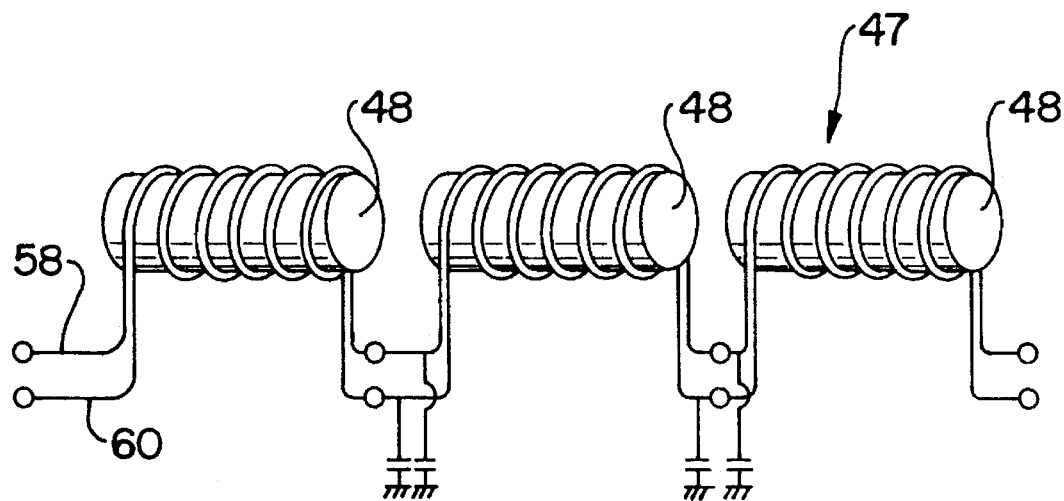
FIG. 5 is a schematic drawing of a band rejection filter network that may be used with the balloon catheter of the invention as a paasive filter.

Referring to FIG. 5, one embodiment of the passive filter 47 is illustrated, in which a band rejection filter is employed as the passive filter 47. The band rejection filter is constructed by multiply winding double cords, such as external insulated lead wires 58, 60 around a ferrite core 48. For example, as is illustrated in FIG. 5, the double cords of two meters length are wound around the core 48 six turns so that rejection frequency may be adjusted to 13.56 MHz.

Figure 6:
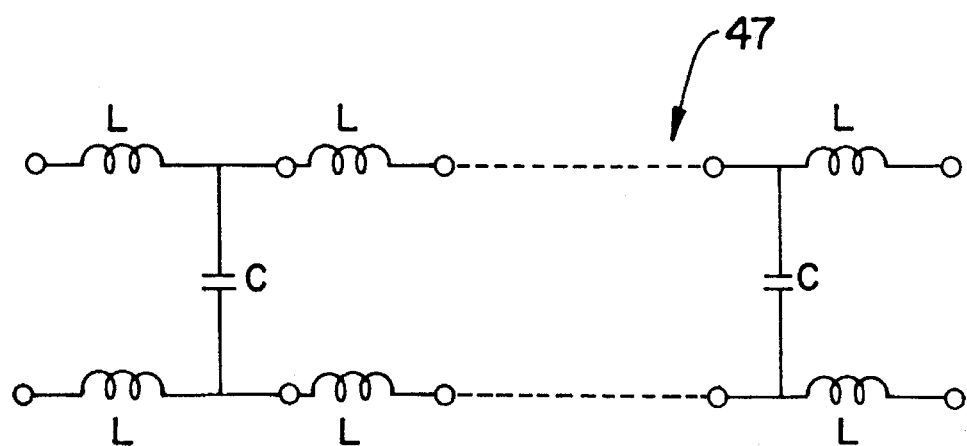
FIG. 6 is schematic drawing of a low-pass filter network that may be used with the balloon catheter of the invention as a passive filter.

Referring to FIG. 6, another embodiment of the passive filter 47 is illustrated, in which low-pass filter is employed as the passive filter 47, illustrating inductance L and capacitance C. In order to improve the electrical conductance from the internal electrode 40 across the balloon into the body, the inflating fluid for the balloon may be 0.9% sodium chloride water solution, or angiographic reagent. In general, the diameter of the balloon 16 should be in the range of from 1.5 mm to 10.0 mm, while PTCA applications with balloons of 2.0 to 2.5 mm and 3.5 mm to 4.0 mm are commonly used.

While, as hereinafter will be described, copper wire has poor mechanical strength, which is prone to be broken in using a fine one. Therefore, high-stiffness metallic wire usually used for guide wire, such as stainless steel wire of iron-like metal, platinum-rhodium wire, tungsten wire, or nitrol wire is employed as the other of electrical conductors of said thermocouple. It should be noted that it is the present inventor alone all around the world who utilizes the above art for thermal PTCA catheter. In this case, these metallic wires have high resistance in general, therefore, electrical conductivity must be improved by plating gold or the like thereon. Otherwise, they are not suitable for electrical conductors for hot balloon catheter employing a two-wire heating system.

Again, referring to FIG. 1, reference numbers 49, 49' are connectors from the internal thermocouple 32 to the external temperature meter 36.

The heating electrode 40 is connected to the R.F. generator 44 via the copper wire 34 and the external insulated lead wire 54, while the electrode 42 external of the patient body is also connected to the R.F. generator 44 via the external insulated lead wire 56. Reference number 50 designates an impedance matching device employing an impedance tuning circuitry for controlling the impedance between the output terminal of said R.F. generator 44 and electrodes 40,42. And reference number 52 designates a phase monitor device of radio frequency electromagnetic wave.

An ordinary oscilloscope may be used as the aforesaid phase monitor or the temperature display of the external temperature controller may be used instead. If the display of the temperature controller is used, the proper phase relationship may be achieved by taking advantage of the inventor's finding such that when the phases at the heating electrode 40 and external electrode 42 are fine-tuned by means of the impedance matching device 50 so that the phase difference at the temperature sensor is adjusted to the maximum, then the temperature rises rapidly.

In accordance with the structure thus made, one can tune the impedance matching device 50 by observing the phase monitor device 52 so that the capacitive current may flow through within a patient's body, thereby local heating can be carried out in the manner of capacitive heating.

Referring to FIG. 3, a section on line 2—2 of the three-passage catheter tube 16' is illustrated. Into the passage 28 are inserted the copper wire 34 connected to the heating electrode 40 as a heating electrical conductor, the copper wire 37 and the constantan wire 38 as the paired electrical conductors connected to the themocouple 32 respectively. FIG. 3 further illustrates a fluid source 26a and a pressurizing pump 26b with a valve means 26c for controlling the liquid flow and direction of the fluid.

In order to connect the thermometer 32 and the external temperature meter 36, the copper wire 37 is connected to the external temperature meter 36 via the connector 49 and the external insulated lead wire 58, while the constantan wire 38 is connected to the same via the connector 49' and the external insulated lead wire 60. Between the thermocouple 32 and external temperature meter 36 is intervened the passive filter 47 as a noise filtering means, whereas the active filter 46 is connected to the external temperature meter 36.

Incidentally, the connector 49 and external insulated lead wire 58 should be fabricated of the same material as that of the constantan wire 38. whereas the connector 49' and external insulated lead wire 60 should be fabricated of the same material as that of the copper wire 37.

Hereinafter is explained the dilatation of the stenosis 12 by the operation of the heated balloon catheter of the present invention.

With the balloon 16 deflated, the catheter is percutanously inserted into an artery 11. After positioning the distal end of the catheter at the stenosis 12, high radio frequency supplied from the R.F. generator 44 is allowed to flow through the patient body across the electrodes 40,42, whereby said heating electrode 40 capacitively heats the stenosis 12 which may be heated to approximately 39–62 degs. for not more than three minutes.

However, for 13.56 MHz radio frequency current, unlike for comparatively low frequnecy current such as about 500 KHz, electric power cannot be applied to the output circuitry (including the catheter in this case) and uselessly consumed within a oscillator output transistor without the impedance matching of said output circuitry. Therefore, it is necessary that the impedance matching operation be performed in the oscillator output circuitry by means of said impedance matching device 50 so that the travelling wave will be maximum while the retreating wave will be minimum therein, and which is obvious to those skilled in the art.

Neverthelss, the present inventor has found that for the maximum dissipation of electric power at the position of balloon 16, it is imperative that more minute matching operation be needed in order to fine-tune the phase of radio frequency power. Only after such fine tuning, can steady heating be obtained.

The stenosis 12 can be heated in such a manner as descrived above. At the same time, into the balloon 16 is fed pressure fluid from a source of fluid 26a through the passage 26 in order to inflate the balloon 16. On the other hand, from the thermocouple 32 is supplied D.C. thermoelectric potential corresponding to the temperature thereof for the external temperature meter 36, in which case, 13.56 MHz R.F. noise will be rejected by means of the passive fliter 47 and active filter 46, so that the proper temperature will be displayed upon the external temperature meter 36.

With the structure and components thus far described, one can heat the inside of the balloon to 39–62 degs. monitoring the external temperature meter 36 so that the balloon 16 can be inflated with the stenosis 12 being moderately heated. Consequently, the stenosis 12 can be sucussfully dilated to ensure the flow of the blood within the artery 11. Further, the capacitive heating between the comparatively small internal electrode 40 and the comparatively large external electrode 42 by the 13.56 MHz R.F. allows the heated-temperature distribution to be biased toward the small internal electrode 40. Therefore, the stenosis 12 can be more effectively and more deep thereinto heated than conventional ones which heat the heating electrode itself.

Referring to FIGS. 7 to 10, another embodiment of the heated balloon catheter of the present invention is illustrated, having two electrical conductor wires therein, in which the same portions as those of the foregoing embodiment are designated as the common reference numbers, and their repeated detail description will be omitted.

As shown in FIGS. 7 and 8, the heating electrical conductor or the copper wire 34 is connected to the heating electrode 40 via the connector 34 A, whereas the distal end of the copper wire 34 is connected to the thermocouple 32. Thus, one straight wire can be used both as a heating electrical conductor and one of the paired electrical conductors connected to the thermocouple 32.

Further, the other of the paired electrical conductors connected to the themocouple 32 employs the constantan wire 38. Then, the distal end of the copper wire 34 is welded to said constantan wire 38 in order to fabricate the thermocouple 32.

In this case, one electrical conductor (which corresponds to said copper wire 34) having comparatively low resistance is used both for heating and temperature measurement, and must be as straight as possible because the electrical conductor or the copper wire 34 has high conductance to the 13.56 MHz power.

On the contrary, the other electrical conductor or the constantan wire 38 having comparatively high resistance is exclusively used for temperature measurement, which has preferably as high radio frequency impedance as possible. Therefore, it is desirable that said constantan wire 38 may be densely coiled. The above-mentioned structures will be indispensable requisites for realizing the present two-wire catheter.

Figure 9:
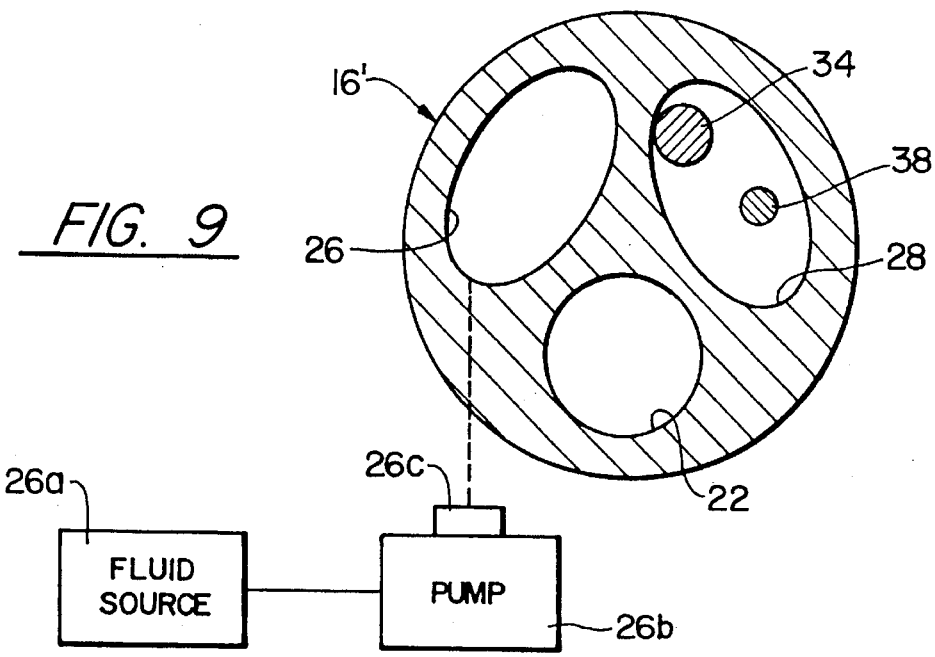
FIG. 9 is a section on line 3—3 of FIG. 7.

Referring to FIG. 9 showing a section on line 3—3 of FIG. 7, into the passage 28 are inserted the copper wire 34 connected to both the heating electrode 40 and the thermocouple 32, the constantan wire 38 connected to the thermocouple 32 as the other electrical conductor.

Figure 10:
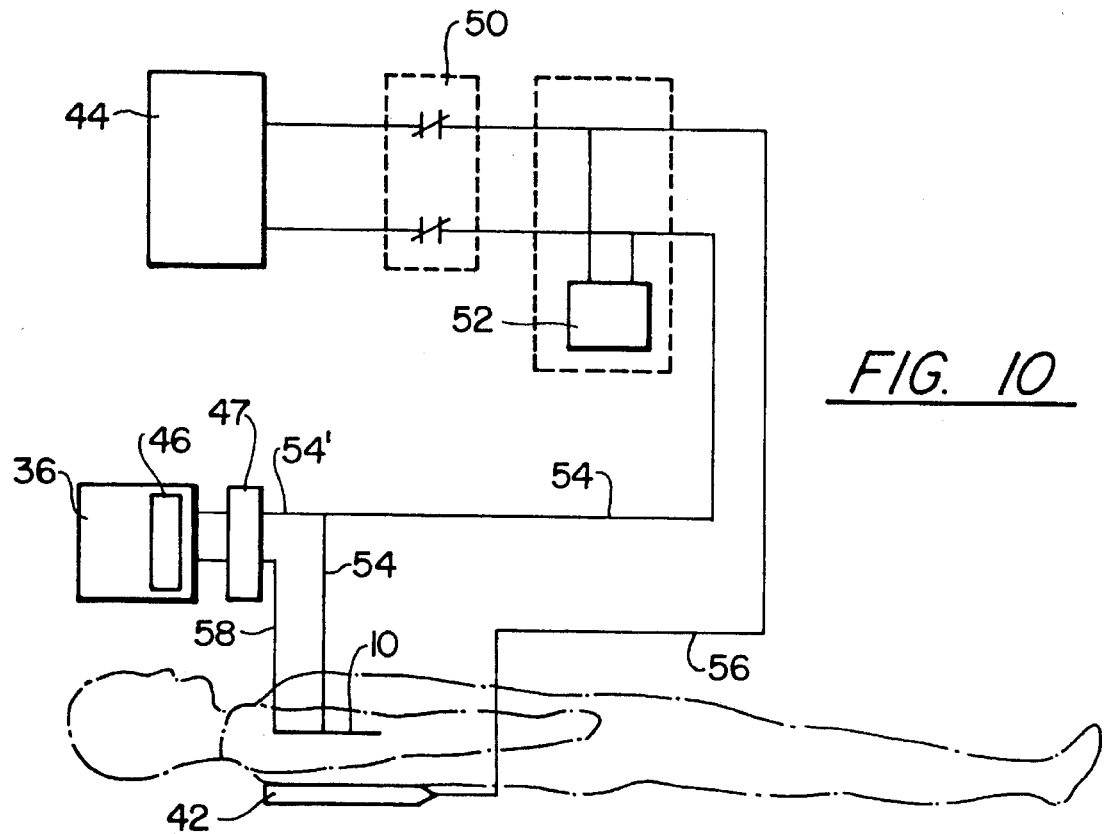
FIG. 10 is a schematic drawing showing the electrical components of the system in relationship to a human undergoing PTCA treatment of the second embodiment.

Referring to FIGS. 7 and 10, to the copper wire 34 is connected to the external insulated lead wire 54, which is connected to the R.F. generator 44 and is shunt-connected to the external insulated shunting lead wire 54', which is further connected to the external temperature meter 36, to which, on the other hand, is connected the constantan wire 38 via the connector 49 and the external insulated wire 58. Between the thermocouple 32 and the external temparature meter 36 is intervened the passive filter 47 as a noise filtering means, whereas the external temperature meter 36 is coupled with the active filter 46.

13.56 MHz R.F. from the R,F. generator 44 is supplied to the heating electrode 40 and the electrode 42 through a straight copper wire 34 and the external insulated wires 54,56 respectively, whereby the capacitive heating can be caused to heat the stenosis 112 to approximately 39–62 degs. for not more than three minutes. At the same time, into the balloon 16 is fed pressurizing fluid from the source of fluid 26a via the lumen 26 to inflate the balloon 16. On the other hand, the thermocouple 32 is connected to the noise filtering means or the passive filter 47, thus 13.56 MHz noise can be rejected so that only the D.C. thermoelectric potential corresponding to the temperature may be output to the external temperature meter 36, while the R.F. noise must be rejected by means of the active rejection filter 46 coupled with the external temperature meter 36.

As hereinbefore described, a straight wire is used both as one electrical conductor connected to the thermocouple 32 and heating electrical conductor, in other words, the copper wire 34 is connected to both the heating electrode 40 and the thermocouple 32, whereas the passive filter 47 is employed to reject 13.56 MHz R.F. noise in said constantan wire 38, whereby two electrical conductors inserted into the catheter tube 16' can perform both heating and temperatrue measurement. Additionally, the catheter is able to be more easily fabricated.

In FIGS. 11 to 14 showing a heated balloon catheter including two electrical conductor wires therein, the same portions as those of the foregoing embodiments are designated as the common reference numbers, and the repeated detail description will be omitted.

Figure 12:
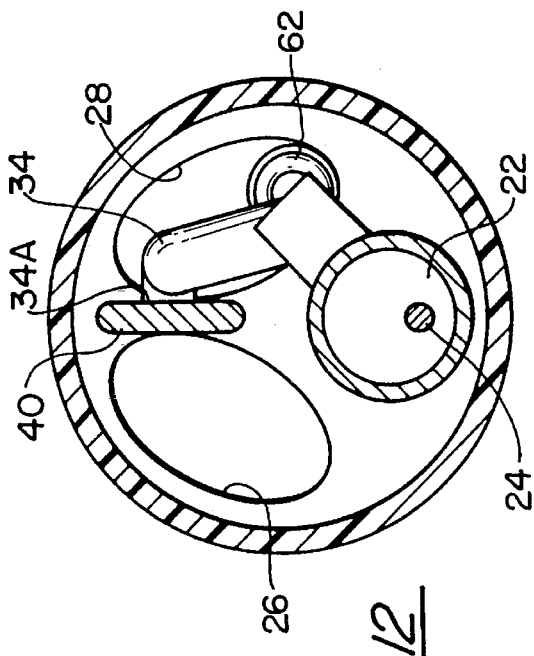
FIG. 12 is a section of the distal end of the catheter of the third embodment.
Figure 11:
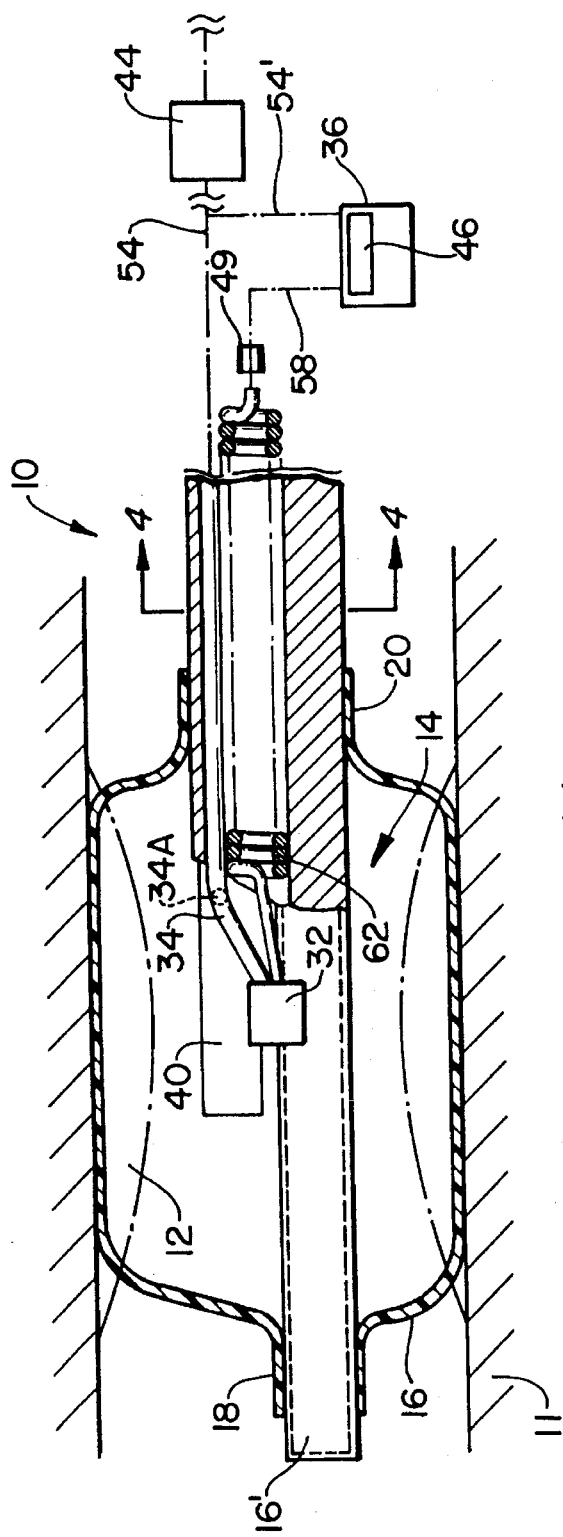
FIG. 11 is a fragmentary sectional view of the distal end of the thermal PTCA balloon catheter of the third embodiment, including two wires therein, also illustrating certain of the electrical components such as the R.F. generator and temperature controller.
Figure 11A:
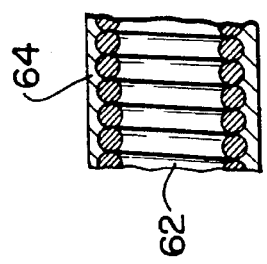
FIG. 11a is an enlarged section of a coil of the third embodiment.

As shown in FIGS. 11 and 12, the heating electrical conductor wire or the copper wire 34 is connected to the heating electrode 40 via the connector 34A, while the distal end of the copper wire 34 is connected to the thermocouple 32, thus one straight wire is used both as the heating electrical conductor and one of the paired electrical conductors connected to the thermocouple 32.

A stainless steel coil 62 of approximately 500 microns I.D. is used as the other electrical conductor of the thermocouple 32 in order to reject the R.F. noise, then the stainless steel coil 62 is inserted into the lumen 26 of the catheter tube 16'.

The stainless steel coil 62 is fabricated by densely winding an insulated stainless steel wire of from 10 to 100 microns diameter so that the diameter of the coil may be 100 to 500 microns. On the surface of the stainless steel coil 62 is formed a coating 64 of polyurethane or the like. The stainless steel coil 62 is approximately 150 centimeters long, preferably nearly as long as the catheter tube 16'. And the distal end of the stainless steel coil 62 is connected to the thermocouple 32. This means that the thermocouple 32 is fabricated by welding the distal end of the copper wire 34 to the stainless steel coil 62. Further, the proximal end of the stainless steel coil 62 is connected to the external temperature meter 36 via the connector 49 and the external insulated lead wire 58.

Figure 13:
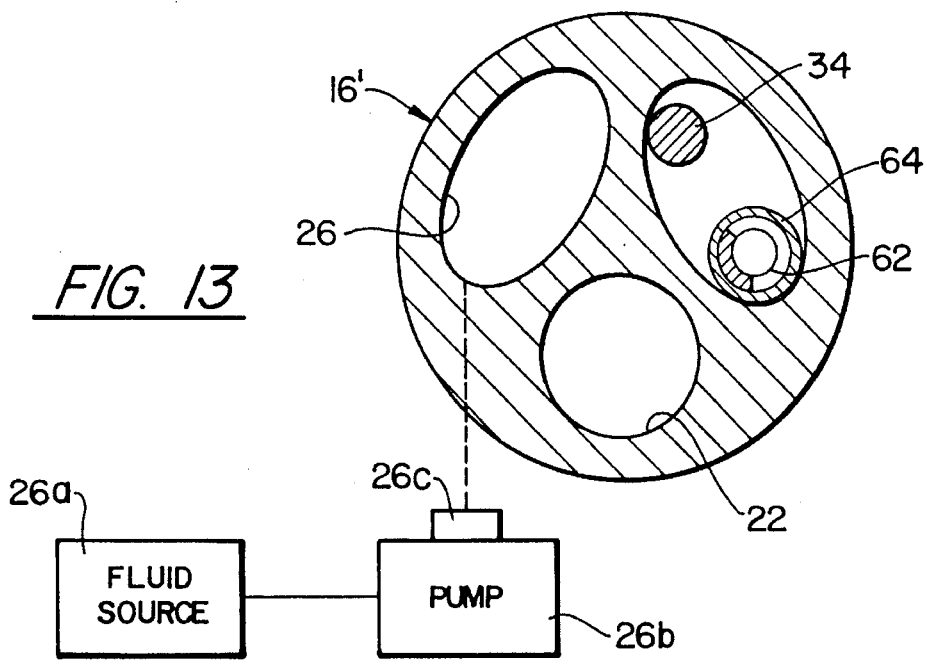
FIG. 13 is a section on line 4—4 of FIG. 11.
Figure 14:
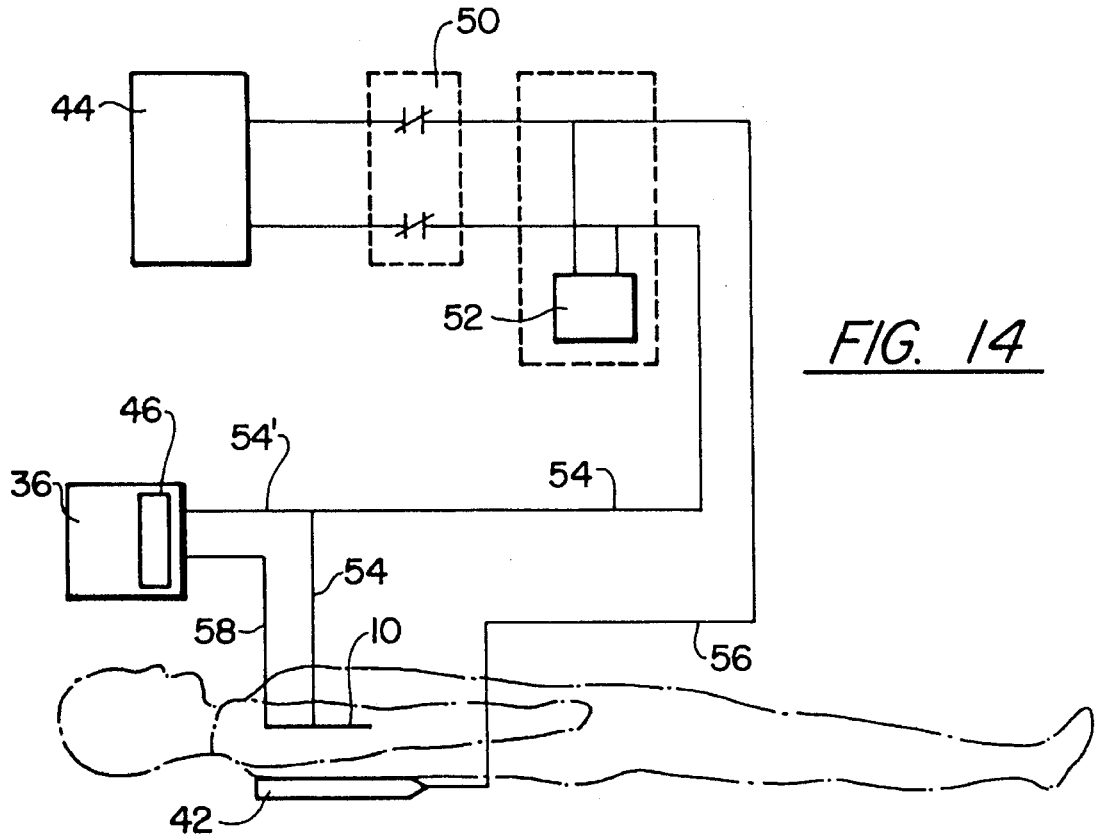
FIG. 14 is a schematic drawing showing the electrical components of the system in relationship to a human undergoing PTCA treatment of the third embodiment.

Referring to FIG. 13, a section on 4—4 line of the FIG. 11 is illustrated, and into the passage 28 are inserted the copper wire 34 and the stainless steel coil 62.

Again referring to FIGS. 11 and 14, the copper wire 34 is connected to the external insulated lead wire 54, which is connected to the R.F. generator 44 and is shunt-connected to the external insulated shunting lead wire 54', which is further connected to the external temperature meter 36. And the external temperature meter 36 is coupled with the active filter 46.

As hereinbefore described, the stainless steel coil 62 is employed as the other electrical conductor connected to the thermocouple 32. Alternatively, a constantan wire may be coiled, in which case, the thermocouple is fabricated by coupling the copper wire and the constantan wire.

13.56 MHz R.F. from the R,F. generator 44 is supplied to the heating electrode 40 and the electrode 42 through a straight copper wire 34 and the external insulated wires 54,56 respectively, whereby the capacitive heating can be caused to heat the stenosis 12 to approximately 39–62 degs. for not more than three minutes. At the same time, into the balloon 16 is fed pressurizing fluid from the source of fluid 26a via the lumen 26 to inflate the balloon 16. On the other hand, the thermocouple 32 is connected to the noise filtering means or the passive filter 47 via the copper wire 34 and the stainless steel wire 62 to the external temperature meter 36, thus 13.56 MHz noise can be rejected by means of the stainless steel coil 62 having a large R.F. inductance so that only the D.C. thermoelectric potential corresponding to the temperature may be output to the external temperature meter 36, while the R.F. noise must be further attenuated by means of the active rejection filter 46 coupled with the external temperature meter 36.

As hereinbefore described, one straight wire is used both as one of the paired electrical conductors connected to the thermocouple 32 and the heating electical conductor, in other words, the copper wire 34 is connected to both the heating electrode 40 and the thermocouple 32, whereas the noise filtering means or the stainless steel coil 62 is employed as the other electrical conductor connecting to the thermocouple 32, thus two electrical conductor wires inserted into the catheter tube 16' can perform both the heating and the temperature measurement. Consequently, the catheter is capable of being more easily fabricated. Further, as the stainless steel coil 62 is housed within the catheter tube 16', neither the bending nor deformation thereof will occur even in heating the catheter tube 16'.

Figure 15:
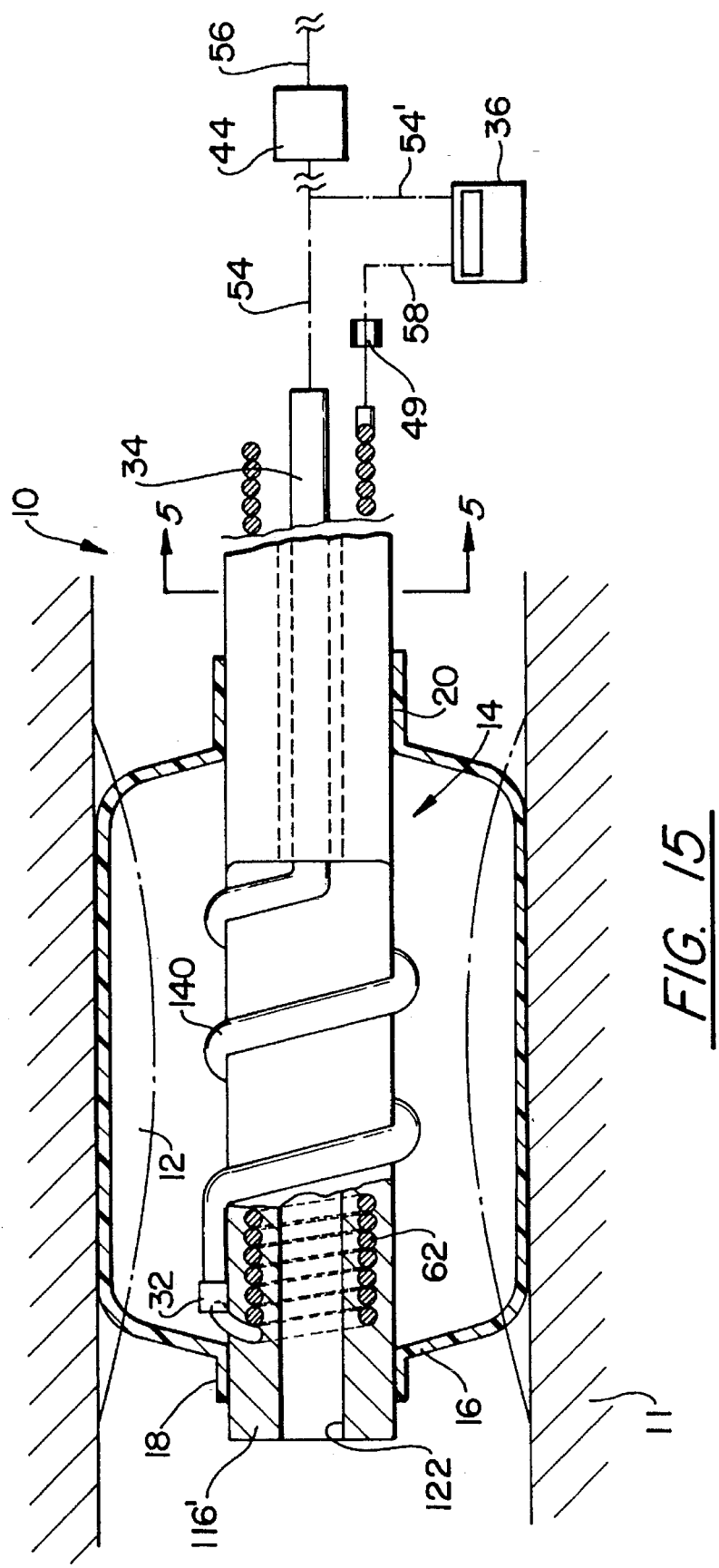
FIG. 15 is a fragmentary sectional view of the distal end of the thermal PTCA balloon catheter of the fourth embodiment, including two wires therein, also illustrating certain of the electrical components such as the R.F. generator and temperature controller.
Figure 16:
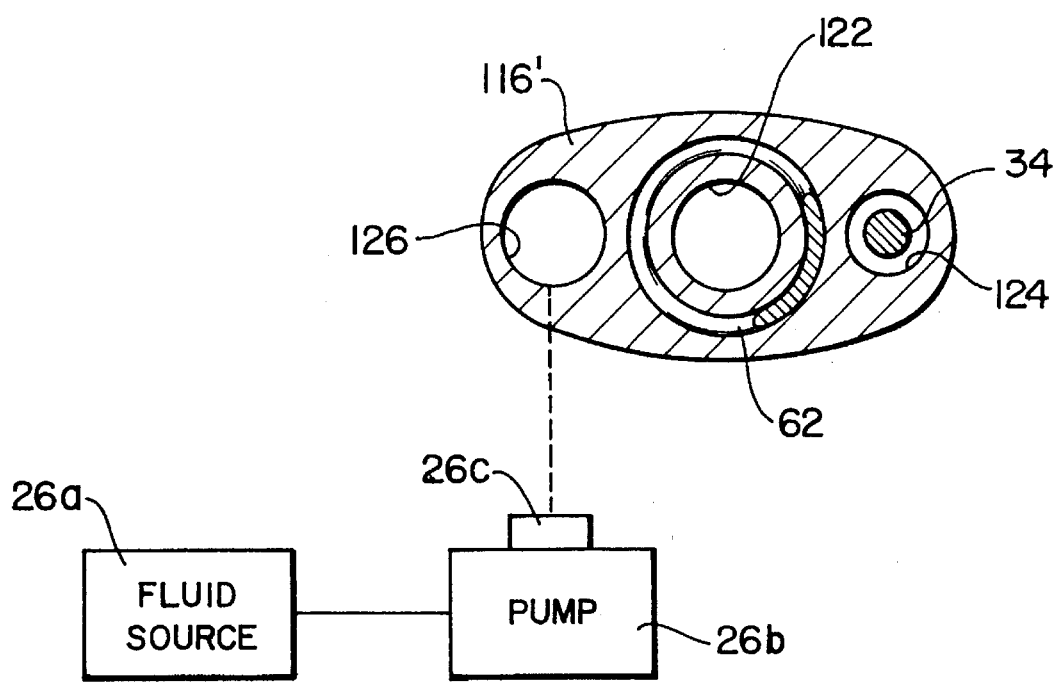
FIG. 16 is a section on line 5—5 of FIG. 15.

Referring to FIGS. 15 and 16, the disclosed heated balloon catheter includes only one straight electrical conductor wire therein, in which a straight electrical conductor wire is incorporated into the catheter, and again the same portions as those forgoing FIGS. 1 to 14 are designated as the common reference numbers, and the repeated detail description will be omitted.

In FIG. 16 showing a three-passage catheter, of which the configurations are approximately oval. To the lumen 126 are connected the source of fluid 26a and the pressurizing pump 26b, having valve means 26c for control of the amount and direction of the fluid flow. And the center passage is a passage for a guide wire, designated as 122. The guide wire passage 122 is integrally provided with the stainless steel coil 62. And into the passage 128 is inserted the heating electrical conductor or the copper wire 34.

The copper wire 34 is provided with the heating electrode 140 coiled around on the surface of the catheter tube 116' in the balloon 14. Within the balloon 14 is provided the thermocouple 32, which is fabricated by welding the stainless steel coil 62 to the copper wire 34, whereby the heating electrode or the copper wire 34 is used as one electrical conductor of the thermocouple 32, whereas the other electrical conductor thereof is structured as the stainless steel coil 62.

Alternatively, a coil fabricated by densely winding a constantan wire can be employed instead of the stainless steel coil 62, in which case, the thermocouple is fabricated by coupling the copper wire and the constantan wire.

The proximal end of the stainless steel coil 62 is connected to the external temperature meter 36 via the connector 49 and the external insulated lead wire 58 respectively. And to the copper wire 34 is connected the external insulated lead wire 54, which is connected to the R.F. generator 44 and is shunt-connected to the external insulated shunting lead wire 54', which is further connected to the external temperature meter 36. Furthermore, the external electrode 42 (not shown in FIGS. 15,16) is connected to the external insulated lead wire 56 connecting to the R.F. generator 44.

13.56 MHz R.F. energy from the R,F, generator 44 is supplied to the heating electrode 140 and the electrode 42 through the straight copper wire 34 and the external insulated lead wires 54,56 respectively, whereby the capacitive heating can be caused to heat the stenosis 12 to approximately 39–62 degs. for not more than three minutes. At the same time, into the balloon 16 is fed pressurizing fluid from the source of fluid 26a via the passage 26 to inflate the balloon 16. On the other hand, the thermocouple 32 is connected to the external temperature meter 36 via the copper wire and the stainless steel wire 62 respectively, thus 13.56 MHz R.F. noise can be rejected by means of the stainless steel coil 62 having a large R.F. inductance so that only the D.C. thermoelectric potential corresponding to the temperature may be output to the external temperature meter 36, while the R.F. noise must be further attenuated by means of the active rejection filter 46 coupled with the external temperature meter 36. Additionally, as the stainless steel coil 62 is incorporated within the catheter body along nearly the whole longitudinal length thereof, the flexibility of the stainless steel coil 62 prevents the catheter tube 116' from being bent or deformed.

Figure 17:
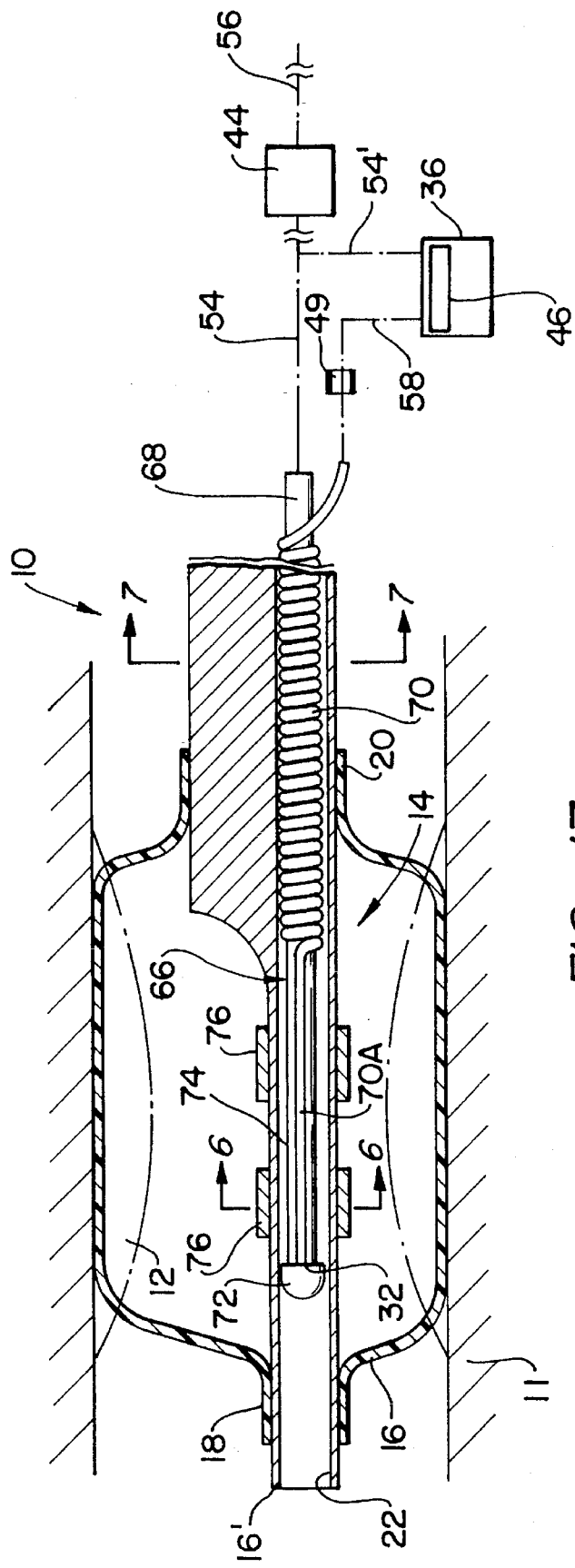
FIG. 17 a fragmentary sectional view of the distal end of the thermal PTCA balloon catheter of the fifth embodiment, including no wires therein, instead of which a guide wire performs both the heating and temperature measurement, also illustrating certain of the electrical components such as the R.F. generator and temperature controller.
Figure 18:
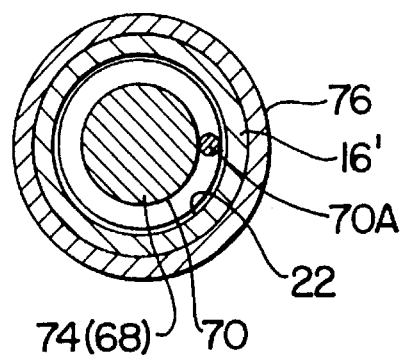
FIG. 18 is a section on line 6—6 of FIG. 17.
Figure 19:
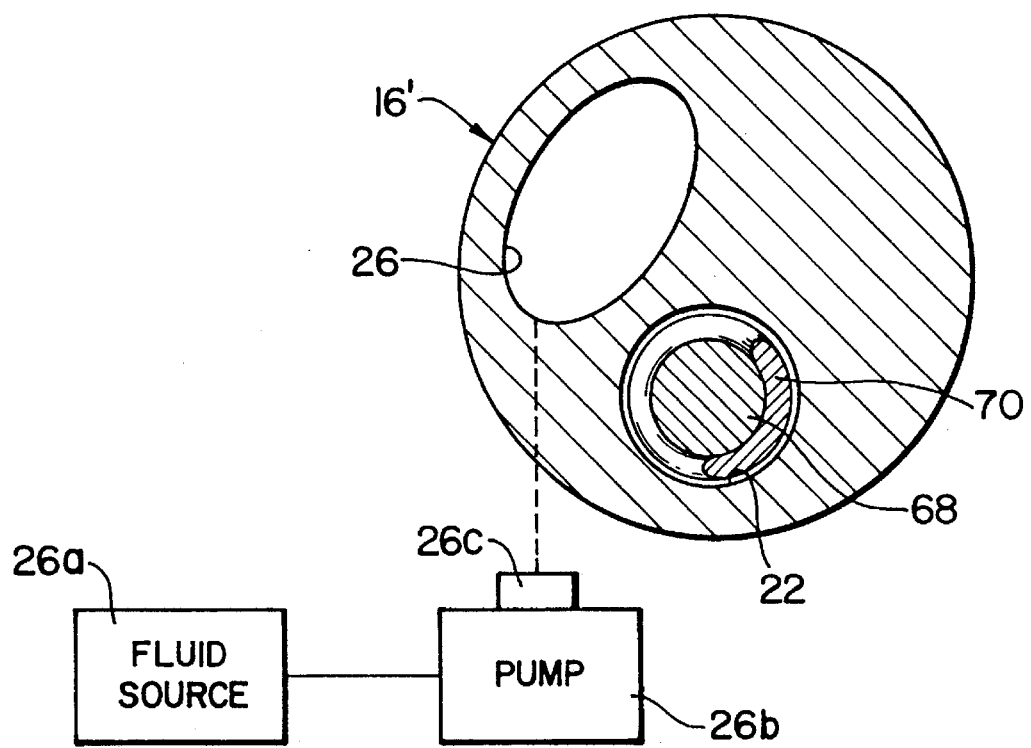
FIG. 19 is a section on line 7—7 of FIG. 17.

In FIGS. 17 to 19 showing a heated balloon catheter of the present invention, which employs no wires within a catheter body, whereas a guide wire for operation of the catheter is used both as the heating means and the temperature sensor.

Referring to FIG. 17, 66 desigantes a guide wire inserted into the guide wire passage 22. The guide wire 66 comprises; a straight mandril 68 to provide the pushability and maneuverability for the catheter, said mandril being made of stainless steel; a coil covering along approximately the whole length of said mandril to provide flexibility and maneuverability, said coil covering being made of a constantan wire.

The straight mandril 66 and the coil covering 70 are insulated each other. And at the distal end of the straight mandril 66 is integrally provided a stainless steel tip 72, while at the distal end of the coil covering 70 is formed a straightened portion 70A, of which the distal end is welded to the tip 72 of the straight mandril 68 to fabricate the thermocouple 32. Further, an exposed portion of the straight mandril 68 where the coil covering 70 is not provided forms an internal electrode 74.

Additionally, around the outside surface of the catheter tube 16' in the balloon 16 is provided a ring-like electromagnetic energy receiver 76 made of metallic material such as gold or platinum, which will be used as X-ray impermeable marker.

Alternatively, a coil covering formed by densely winding a copper wire may be employed instead of the stainless steel coil covering 70, in which case, the thermocouple is fabricated by coupling the copper wire and the stainless steel wire.

Further, the proximal end of the coil covering 70 is connected to the external temperature meter 36 via the connector 49 and the external insulated lead wire 58 respectively. And the straight mandril 68 is connected to the external insulated lead wire 54, which is connected to the R.F. generator 44 and is further shunt-connected to the external insulated shunting lead wire 54', to which is connected the external temperature meter 36. Although not shown in FIGS. 17 to 19, said external insulated lead wire 56 connected to the R.R. generator 44 is connected to the external electrode 42. Incidentally, the connector 49 and the external insulated lead wire 58 are formed of the same material as that of the coil covering 70, whereas the external insulated wires 54 and 54' are formed of the same material as that of the straight mandril 68.

Hereinafter is described the action of the embodiment thus structured.

The guide wire 66 inserted into the catheter body is operated so that the distal end of the catheter is positioned at the constricted zone or the stenosis 12. Then the distal end of the guide wire 66 is aligned to the balloon 16, whereby the internal electrode 74 of the straight mandril 68 is positioned within the electromagnetic energy receiver 76 through the catheter tube 16'.

Then, 13.56 MHz R.F. energy from the R.F. generator 44 is supplied to the internal electrode 74 and the electrode 42 via the straight mandril 68 and the external insulated lead wires 54,56 respectively. Thus, the electromagnetic energy transmitted from the internal electrode 74 is collected by the electromagnetic energy receiver 76, whereby between the electromagnetic energy receiver 76 and the the external electrode 42 is caused the capacitive heating to heat the stenosis 12 to nearly 39–62 degs. for not more than three minutes. At the same time, into the balloon 16 is fed the pressurizing fluid from the source of fluid 26a via the lumen 26 to inflate the balloon 16.

On the other hand, since the thermocoule 32 is connected to the external temperature meter 36 via the straight mandril 68 and the coil covering 70, the coil covering 70 having a large R.F. inductance permits the 13.56 MHz R.F. noise to be rejected so that only the D.C. thermoelectric potential of the thermocouple 32 is output to the external temperature meter 36, corresponding to the temperature of the thermocouple 32. In which case, the active rejection filter 46 must still attenuate the R.F. noise to have a stable temperature reading.

As hereinbefore described, according to the present embodiment of the invention, the straight mandril 68 is used both as the heating electrical conductor and internal electrode within the catheter, while the coil covering 70 is employed as the noise filtering means for the thermocouple 32, thus it is not necessary any longer to insert electrical conductors into the balloon.

That is to say, the electromagnetic energy transmitted from the straight mandril 68 is collected by the electromagnetic energy receiver 76 within the balloon 16, thus the capacitive heating is caused between the electromagnetic energy receiver 76 and the external electrode 42 to heat the stenosis 12. Accordingly, the electrical conductors are no longer necessary in the catheter, instead of which, the guide wire 66 for operation of the catheter can perform both the heating and temperature measuring of the catheter. Further, as the metallic electromagnetic energy receiver 76 is provided within the balloon 16 further to function as X-ray opaque marker, the position of the distal end 14 of the catheter can be easily perceived by means of X-ray photography.

Incidentally, the present invention should not be limited to the embodiments thus far described but can be modified within the scope of the invention. For example, the heated balloon catheter of the present invention may be applied to dilate a narrowing of a heart valve caused by valvular heart disease.

Further, in order to effectively perform the present unipolar heating system across the insulated membrane, the frequency range of 100 KHz to 100 MHz may be possible, however, most effective heating can be attained within a frequency range from 2 MHz to 20 MHz. Accordingly, the present invention may be applied to high oscillation frequency of 2 MHz to 20 MHz. That is because below 2 MHz, the small capacitance of the insulated membrane makes the unipolar heating more and more difficult, whereas above 20 MHz, it becomes difficult to confine the radio wave within the heating conductors.

Furthermore, electrical conductors connected to the thermocouple may be made of various materials other than those shown in the embodiments. For example, platinum resistance thermometer or thermistor sensor may also be employed.

What is claimed:

1. A heated balloon catheter for treatment of constricted zones of body fluid passages by applying heat and pressure to the constricted zones comprising;

a catheter body having a proximal end, a distal end and a plurality of longitudinal passages therethrough;

a balloon secured to the distal end of the catheter, communicating with at least one of said longitudinal passages;

a means for directing pressurized fluid to and from the balloon through said at least one longitudinal passage;

a thermocouple mounted within the balloon;

an external temperature meter;

paired electrical conductors for connecting said thermocouple with said external temperature meter;

an internal heating electrode provided within the catheter;

an external electrode provided outside the catheter;

an R.F. generator for generating a radio frequency in the order of 2 MHz to 20 MHz, said R.F. generator being located outside said catheter as a power source for the capacitive heating of tissues around the balloon;

a first heating electrical conductor electrically connecting said R.F. generator to said internal heating electrode;

a second heating electrical conductor electrically connecting said R.F. generator to said external electrode;

a noise filtering means for rejecting said 2 MHz to 20 MHz R.F. noise in said paired electrical conductors connected with said thermocouple;

and an impedance matching network to fine tune the impedance between said R.F. generator and said internal and external electrodes, said impedance matching network being interposed between said R.F. generator and said internal and external electrodes.

2. A heated balloon catheter according to claim 1, wherein said external temperature meter is connected to an active rejection filter to reject the 2 MHz to 20 MHz R.F. noise.

3. A heated balloon catheter according to claim 1, wherein at least one of said paired electrical conductors for connecting said thermocouple with said external temperature meter, is a metallic wire with high stiffness such as iron wire.

4. A 2 MHz to 20 MHz radio frequency heating system in use for hot balloon PTCA catheter described in claim 1, wherein the transformation of the 2 MHz to 20 MHz radio frequency energy into heat can be maximized by observing the temperature rise within the balloon indicated by said temperature meter, and by controlling the output impedance matching means in order that the phase difference in 2 MHz to 20 MHz radio frequency signal between said first heating electrical conductor and said second heating electrical conductor may be maximized.

5. A 2 MHz to 20 MHz radio frequency heating system in use for hot balloon PTCA catheter described in claim 1, wherein the transformation of the 2 MHz to 20 MHz radio frequency energy into heat can be maximized by observing the electromagnetic wave forms of the 2 MHz to 20 MHz radio frequency signals from said first and said second heating electrical conductors by means of an oscillographic display, and by controlling the output impedance matching means in order that the phase difference in 2 MHz to 20 MHz radio frequency signal between said first heating electrical conductor and said second heating electrical conductor may be maximized.

6. A heated balloon catheter for treatment of constricted zones of body fluid passages by applying heat and pressure to the constricted zones comprising;

a catheter body having a plurality of longitudinal passages therethrough;

a balloon secured to the distal end of the catheter, communicating with at least one of said longitudinal passages;

a means for directing pressurized fluid to and from the balloon through said at least one longitudinal passage;

a thermocouple mounted within the balloon;

an external temperature meter;

paired electrical conductors for connecting said thermocouple with said external temperature meter;

an internal heating electrode provided within the catheter;

an external electrode provided outside the catheter;

an R.F. generator for generating a radio frequency in the order of 2 MHz to 20 MHz, said R.F. generator being located outside said catheter as a power source for the capacitive heating of tissues around the balloon;

a first heating electrical conductor electrically connecting said R.F. generator to said internal heating electrode;

a second heating electrical conductor electrically connecting said R.F. generator to said external electrode;

a noise filtering means for rejecting said 2 MHz to 20 MHz R.F. noise in the second electrical conductor connected with said thermocouple;

and an impedance matching network to fine tune the impedance between said R.F. generator and said internal and external electrodes, said impedance matching network being interposed between said R.F. generator and said internal and external electrodes, being characterized in that a straight electrical conductor is used both as one of said paired electrical conductors and said first heating electrical conductor, thus said catheter is provided therein with two wires consisting of the other of said paired electrical conductors connected to said thermocouple and the straight electrical conductor.

7. A heated balloon catheter according to claim 6, wherein the other of said paired electrical conductors connected to said thermocouple is provided with electrically inductive means such as a multiply would coil in order to reject 2 MHz to 20 MHz R.F. noise.

8. A heated balloon catheter according to claim 6, wherein metallic wire with high-stiffness such as iron wire is employed for the other electrical conductor connected to said thermocouple.

9. A heated balloon catheter according to claim 6, wherein said external temperature meter is connected to an active rejection filter to reject the 2 MHz to 20 MHz R.F. noise.

10. A 2 MHz to 20 MHz radio frequency heating system in use for hot balloon PTCA catheter described in claim 6, wherein the transformation of the 2 MHz to 20 MHz radio frequency energy into heat can be maximized by observing the temperature rise within the balloon indicated by said temperature meter, and by controlling the output impedance matching means in order that the phase difference in 2 MHz to 20 MHz radio frequency signal between said straight electrical conductor and said second heating electrical conductor may be maximized.

11. A 2 MHz to 20 MHz radio frequency heating system in use for hot balloon PTCA catheter described in claim 6, wherein the transformation of the 2 MHz to 20 MHz radio frequency energy into heat can be maximized by observing the electromagnetic wave form of the 2 MHz to 20 MHz radio frequency signals from said straight electrical conductor and said second heating electrical conductor by means of an oscillographic display, and by controlling the output impedance matching means in order that the phase difference in 2 MHz to 20 MHz radio frequency signal between said first heating electrical conductor and the second heating electrical conductor may be maximized.

12. A heated balloon catheter for treatment of constricted zones of body fluid passages by applying heat and pressure to the constricted zones comprising;

a catheter body having at least one longitudinal passage and a guidewire passage therethrough;

a balloon secured to the distal end of the catheter, communicating with a least one of said longitudinal passages;

a means for directing pressurized fluid to and from the balloon through said at least one longitudinal passage, an internal heating electrode provided within the catheter;

an external electrode provided outside the catheter;

an R.F. generator for generating a radio frequency in the order of 2 MHz to 20 MHz, said R.F. generator being located outside said catheter as a power source for the capacitive heating of tissues around the balloon;

a first heating electrical conductor electrically connecting said R.F. generator to said internal heating electrode;

a second heating electrical conductor electrically connecting said R.F. generator to said external electrode, an impedance matching network to fine tune the impedance between said R.F. generator and said internal and external electrodes, said impedance matching network being interposed between said R.F. generator and said internal and external electrodes;

and a guide wire inserted into said guide wire passage, which is characterized in that said guide wire comprises, a straight mandril to provide the stiffness and maneuverability;

a coil covering provided along nearly the whole length of said mandril to provide flexibility and maneuverability;

a thermocouple welded at a distal end of said guide wire, being characterized in that said thermocouple is connected to an external temperature meter via said straight mandril and coil covering, said straight mandril being connected to 2 MHz to 20 MHz R.F. generator in order to be used as said first heating electrical conductor with a distal end of said straight mandril being used as said internal heating electrode, said coil covering being used as a noise filtering means for rejecting 2 MHz to 20 MHz R.F. noise.

13. A heated balloon catheter according to claim 12, wherein an electromagnetic energy receiver is provided within the catheter so that said receiver can collect the energy transmitted from said straight mandril further to transmit the energy into tissues around the balloon.

14. A heated balloon catheter according to claim 12, wherein said straight mandril is formed of metallic wire with high-stiffness such as iron wire.

15. A heated balloon catheter according to claim 12, wherein said external temperature meter is connected to an active rejection filter to reject the 2 MHz to 20 MHz R.F. noise.

16. A 2 MHz to 20 MHz radio frequency heating system in use for hot balloon PTCA catheter described in claim 12, wherein the transformation of the 2 MHz to 20 MHz radio frequency energy into heat can be maximized by observing the temperature rise within the balloon indicated by said temperature meter, and by controlling the output impedance matching means in order that the phase difference in 2 MHz to 20 MHz radio frequency signal between said straight mandril and said second heating electrical conductor may be maximized.

17. A 2 MHz to 20 MHz radio frequency heating system in use for hot balloon PTCA catheter described in claim 12, wherein the transformation of the 2 MHz to 20 MHz radio frequency energy into heat can be maximized by observing the electromagnetic wave forms of the 2 MHz to 20 MHz radio frequency signals from said straight mandril and said second heating electrical conductor by means of an oscillographic display, and by controlling the output impedance matching means in order that the phase difference in 2 MHz to 20 MHz radio frequency signal between said straight mandril and said second heating electrical conductor may be maximized.

* * * * *